United States Patent [19]
Chen et al.

[11] Patent Number: 6,020,174
[45] Date of Patent: Feb. 1, 2000

[54] CHEMOENZYMATIC SYNTHESIS OF THE TAXOL C-13 SIDE CHAIN N-BENZOLYL-(2R,3S)-PHENYLISOSERINE

[75] Inventors: Ching-Shih Chen, Wakefield; Da-Ming Gou, Kingston, both of R.I.; Yeuk-Chuen Liu, West Lafayette, Ind.

[73] Assignee: The Board of Governors for Higher Education, R.I.

[21] Appl. No.: 08/538,179

[22] Filed: Aug. 23, 1995

Related U.S. Application Data

[63] Continuation of application No. 08/262,346, Jun. 20, 1994, abandoned, which is a continuation of application No. 07/920,003, Jul. 27, 1992, abandoned.

[51] Int. Cl.$^7$ ............................. C12P 13/06; C12P 17/02
[52] U.S. Cl. ......................... 435/123; 435/280; 435/116
[58] Field of Search .................... 435/123, 125, 435/280, 106, 116; 562/553

[56] References Cited

U.S. PATENT DOCUMENTS

| | | | |
|---|---|---|---|
| 4,471,130 | 9/1984 | Katsuki | 549/523 |
| 4,732,853 | 3/1988 | Whitesides | 435/280 |

FOREIGN PATENT DOCUMENTS

| | | |
|---|---|---|
| 0333142 | 9/1989 | European Pat. Off. . |
| 343714 | 11/1989 | European Pat. Off. . |
| 0362556 | 4/1990 | European Pat. Off. . |
| 0417785 | 3/1991 | European Pat. Off. . |
| 0454463 | 10/1991 | European Pat. Off. . |
| 4115697 | 11/1991 | Germany . |

OTHER PUBLICATIONS

Denis, J–N et al., "An Efficient, Enantio selective Synthesis of the Taxol Side Chain," *J. Org. Chem.,* vol. 51, pp. 46–50, 1986.

Denis, J. N. et al., "An Improved Synthesis of the Taxol Side Chain an v) RP56976", *J. Org. Chem.,* vol. 55, pp. 1957–1959, 1990.

Deng et al., "A Practical, Highly Enantioselective Synthesis of the Taxol Side Chain via Asymmetric Catalysis", *J. Org. Chem.,* vol. 57, pp. 4320–4323, 1992.

Bianchi, D. et al., "Enzymatic Resolution of 2.3 epodyalcohols . . . Phermona", *Tetrahedron Letters,* vol. 29, No. 20, pp. 2455–2458, 1988.

Wang, Y et al., "Lepae—Catalyzed Irreversial Transesterifications . . . organometallic", vol. 110, pp. 7200–7205, 1988.

*Primary Examiner*—Irene Marx
*Attorney, Agent, or Firm*—Samuels, Gauthier & Stevens

[57] ABSTRACT

(2R,3S)- and (2S,3R)-enantiomers of trans-β-phenylglycidic esters, prepared by lipase-mediated enantioselective transesterification, are used for the synthesis of the taxol C-13 side chain with good yield.

11 Claims, 11 Drawing Sheets

CHEMOENZYMATIC SYNTHESIS OF THE TAXOL C-13 SIDE CHAIN N-BENZOLYL-(2R,3S)-PHENYLISOSERINE

This a continuation of application(s) Ser. No. 08/262,346 filed on Jun. 20, 1994, now abandoned, which is a continuation of application(s) Ser. No. 07/920,003 filed on Jul. 27, 1992, now abandoned.

BACKGROUND AND BRIEF SUMMARY OF THE INVENTION

Taxol an antimicrotubule agent isolated from the bark of *Taxus brevifolia*, Rowinsky, E. K.; Donehower, R. C., *Pharmac. Ther.* 1991, 52, 35, has recently attracted much attention because of its efficacy in the treatment of various types of cancer, (a) Slichenmyer, W. J.; Van Hoff, D. D., *Anti-Cancer Drugs*, 1991, 2, 519; (b) Rowinsky, E. K.; Donehower, R. C. J., *Natl. Cancer Inst.*, 1991, 83 1778; (c) Holes, F. A.; Walters, R. S.; Theriault, R. L.; Forman, A. D.; Newton, L. K.; Raber, M. N.; Buzdar, A. U.; Frye, D. K.; Hortobagyi G. N., Ibid. 1991, 83, 1797. However, one major impediment to the wide use of taxol in cancer chemotherapy is its extremely limited availability. Also, chemical complexity has prohibited the commercial production of taxol by total synthesis, (a) Kingston, D. G. I.; Samaranayake, G.; Ivey, C. A., J. *Nat. Prod.*, 1990, 53, 1; (b) Kingston, D. G. I., *Pharmac. Ther.*, 1991, 52, 1. Thus, a viable approach for the preparation of taxol is to utilize more accessible baccatin III or 10-deacetylbaccatin III -continued as precursor via a semisynthetic route, (a) Denis, J. -N; Greene, A. E.; Guenard, D.; Gueritte-Voegelein, F.; Mangatal, L.; Potier, P., *J. Am. Chem. Soc.*, 1988, 110, 5917; (b) Holton, R. A., U.S. Pat. No. 5,015,744, (*Chem. Abst.*, 1991, 115, 159485).

As the importance of the C-13 side chain, the N-benzoyl-(2R, 3S)-phenylisoserine, moiety, where R=H or $CH_3$ for the biological activity of taxol becomes evident, (a) Guenard, D.; Gueritte-Voegelein, F.; Lavelle, F.; Le Goff, M. T.; Mangatal, L.; Potier, P., *J. Med. Chem.*, 1991, 34, 992; (b) Swindell, C. S.; Krauss, N. E.; Horwitz, S. B.; Ringel, I., *Ibid*, 1991, 34, 1176, enantioselective synthesis of N-Benzoyl-(2R,2S)-3-Phenylisoserine has been the focus of many investigations. A variety of strategies employing Sharpless epoxidation, Denis, J. -N; Greene, A. E.; Serra, A. A.; Luche, M.-J., *J. Org. Chem.*, 1986, 51, 46, asymmetric dihydroxylation, Denis, J. -N.; Correa, A.; Greene, A. E., *J. Org. Chem.*, 1990, 55, 1957, enzymatic resolution, (a) Honig, H.; Seufer-Wasserthal, P.; Weber, H. *Tetrahedron*, 1990, 46, 3841; (b) Honig, H.; Seufer-Wasserthal; Weber, H., *Tetrahedron Lett.*, 1990, 31, 3011, a chiral precursor, Denis, J. -N.; Correa, A.; Greene, A. E., *J. Org. Chem.*, 1991, 56, 6939, and asymmetric ester enolate-imine cyclocondensation, Ojima, I.; Habus, I.; Zhao, M; Georg. G. I.; Jayasinghe, L. R. *J. Org. Chem.*, 1991, 56, 1681, have been reported.

The present invention embodies a facile approach using enzymatically-prepared chiral trans-β-phenylglycidic esters as the starting material for the synthesis of the taxol C-13 side chain.

DESCRIPTION OF THE PREFERRED EMBODIMENT(S)

Figure 1:
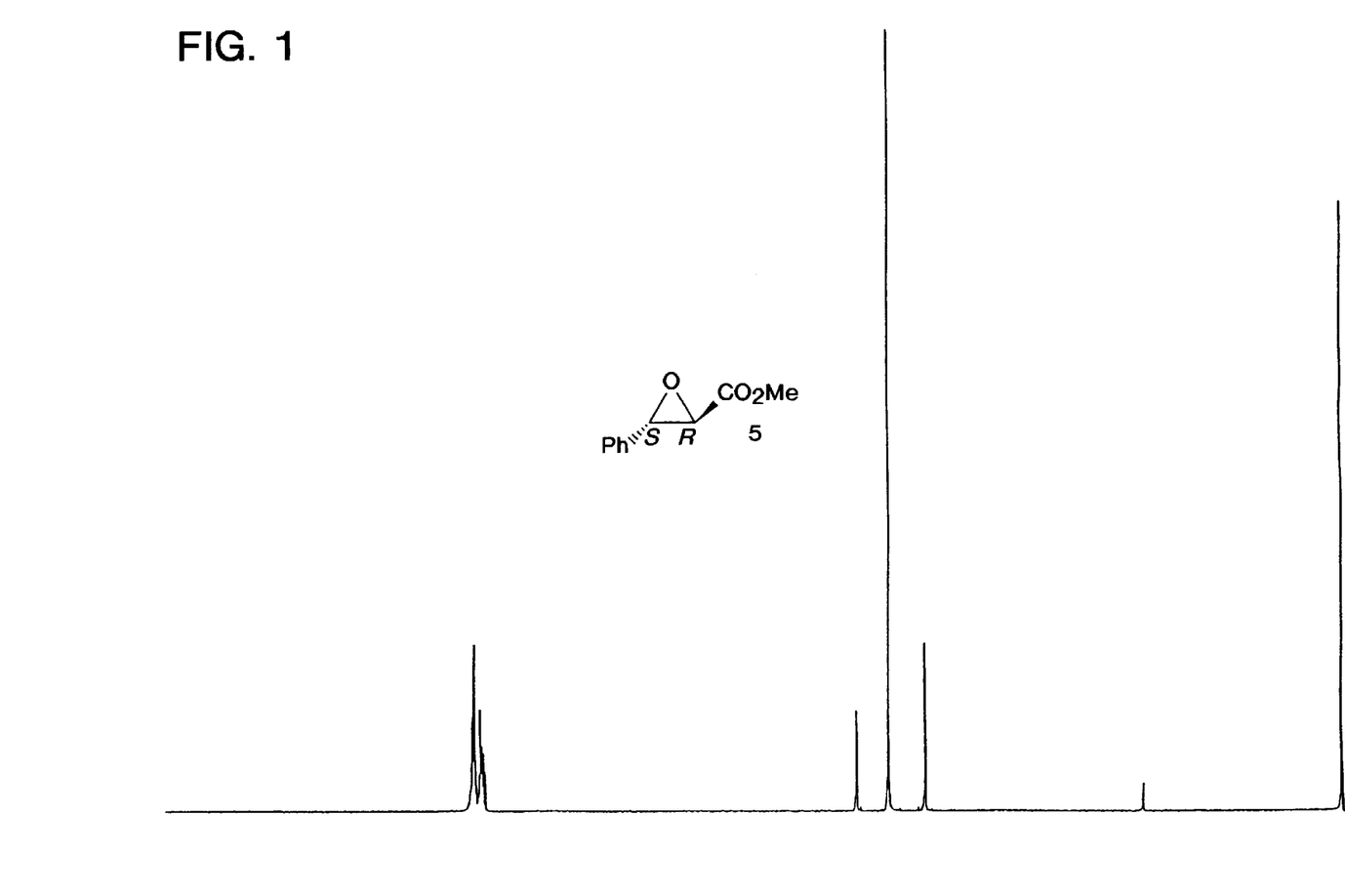
FIGS. 1 through 11 are NMR scans of compounds 5 and 7–16.
Figure 2:
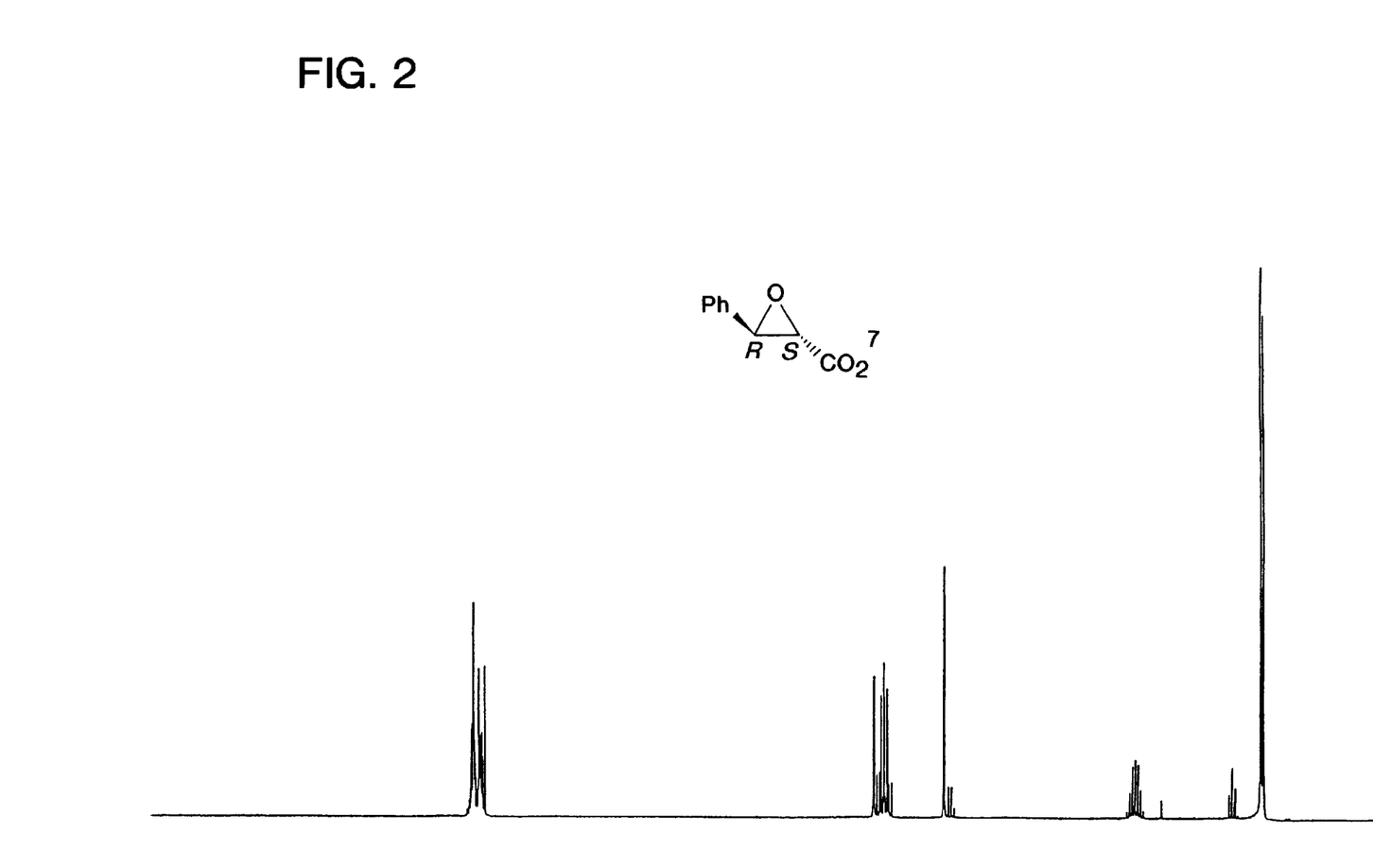
Figure 3:
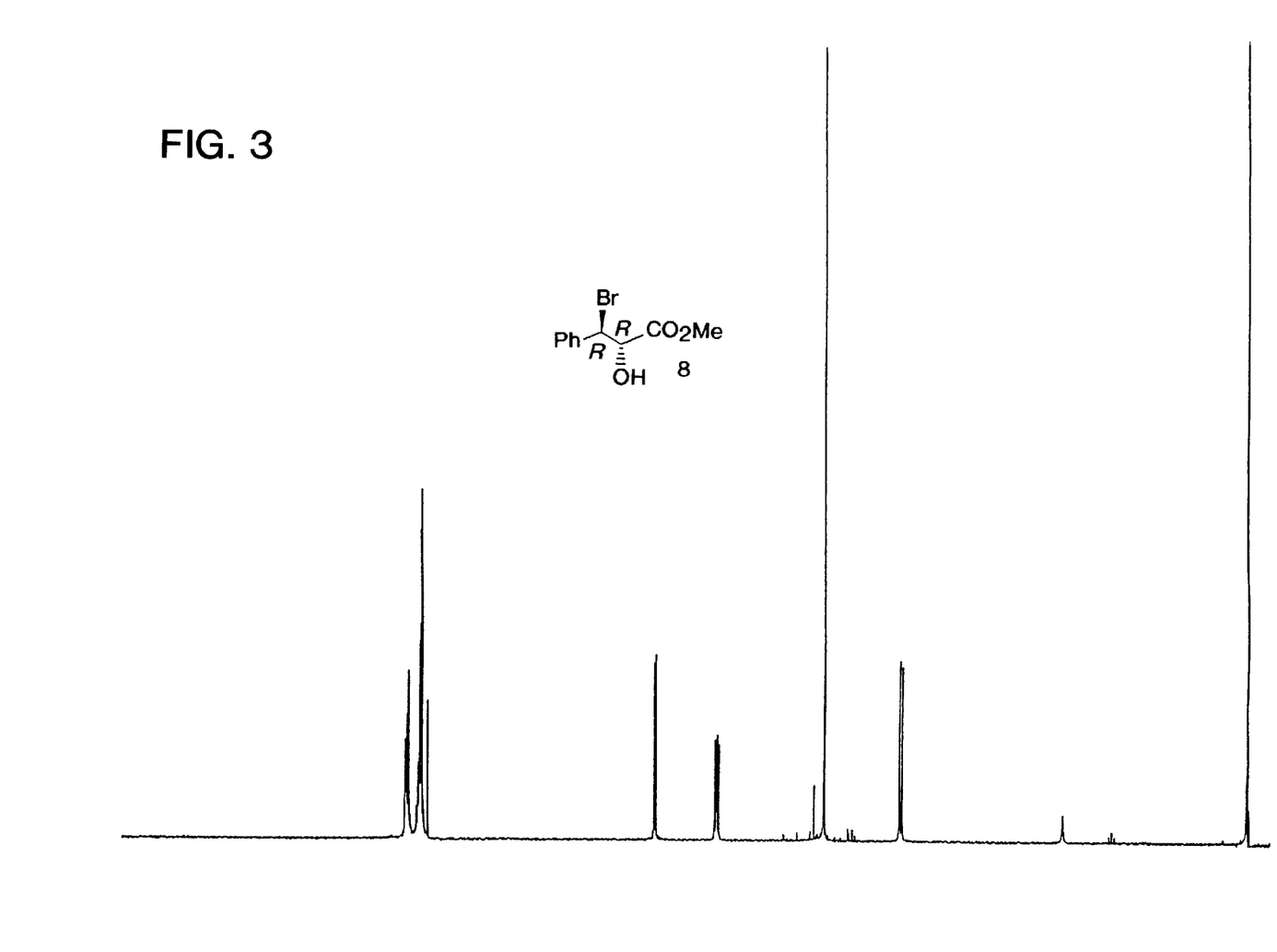
Figure 4:
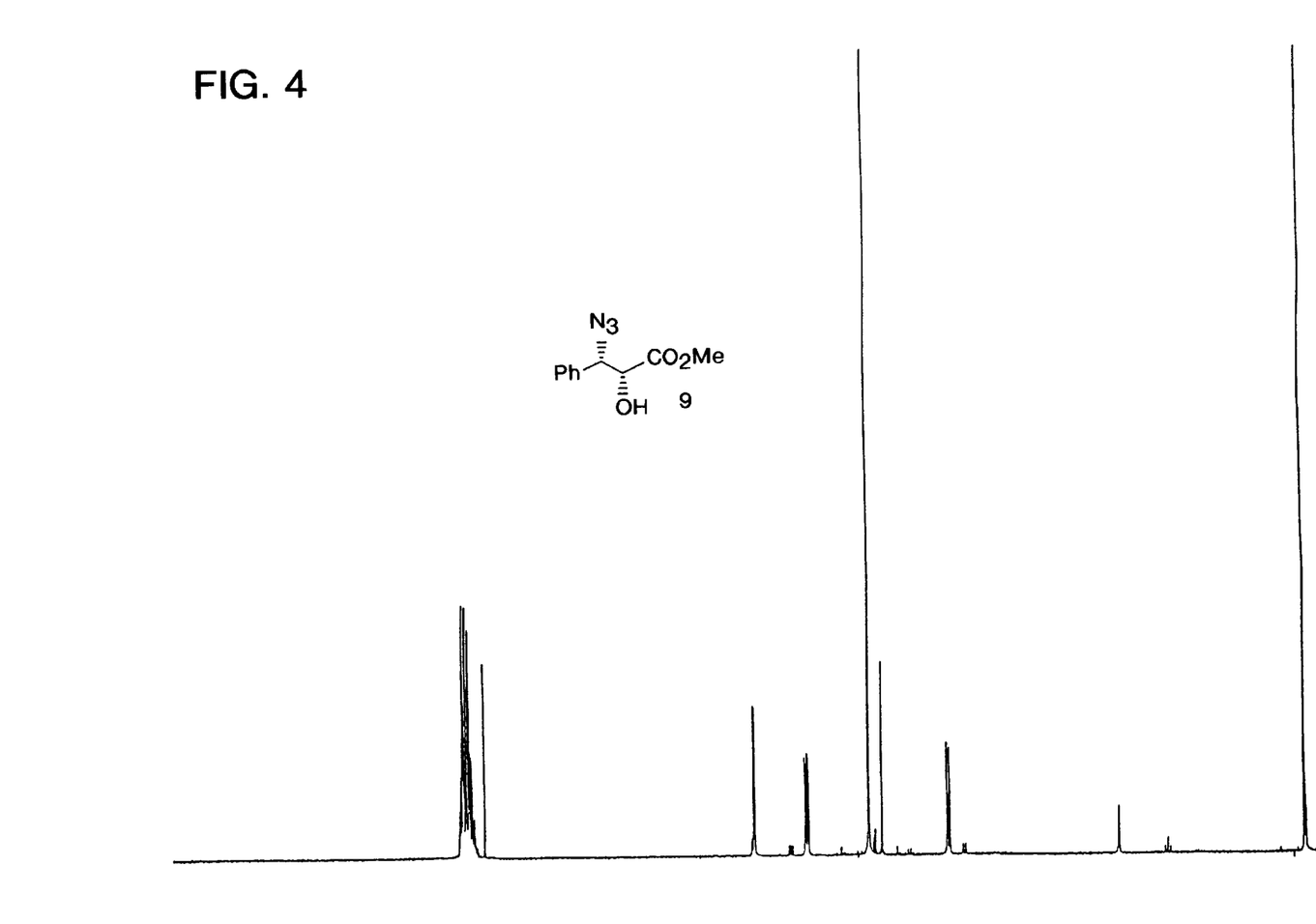
Figure 5:
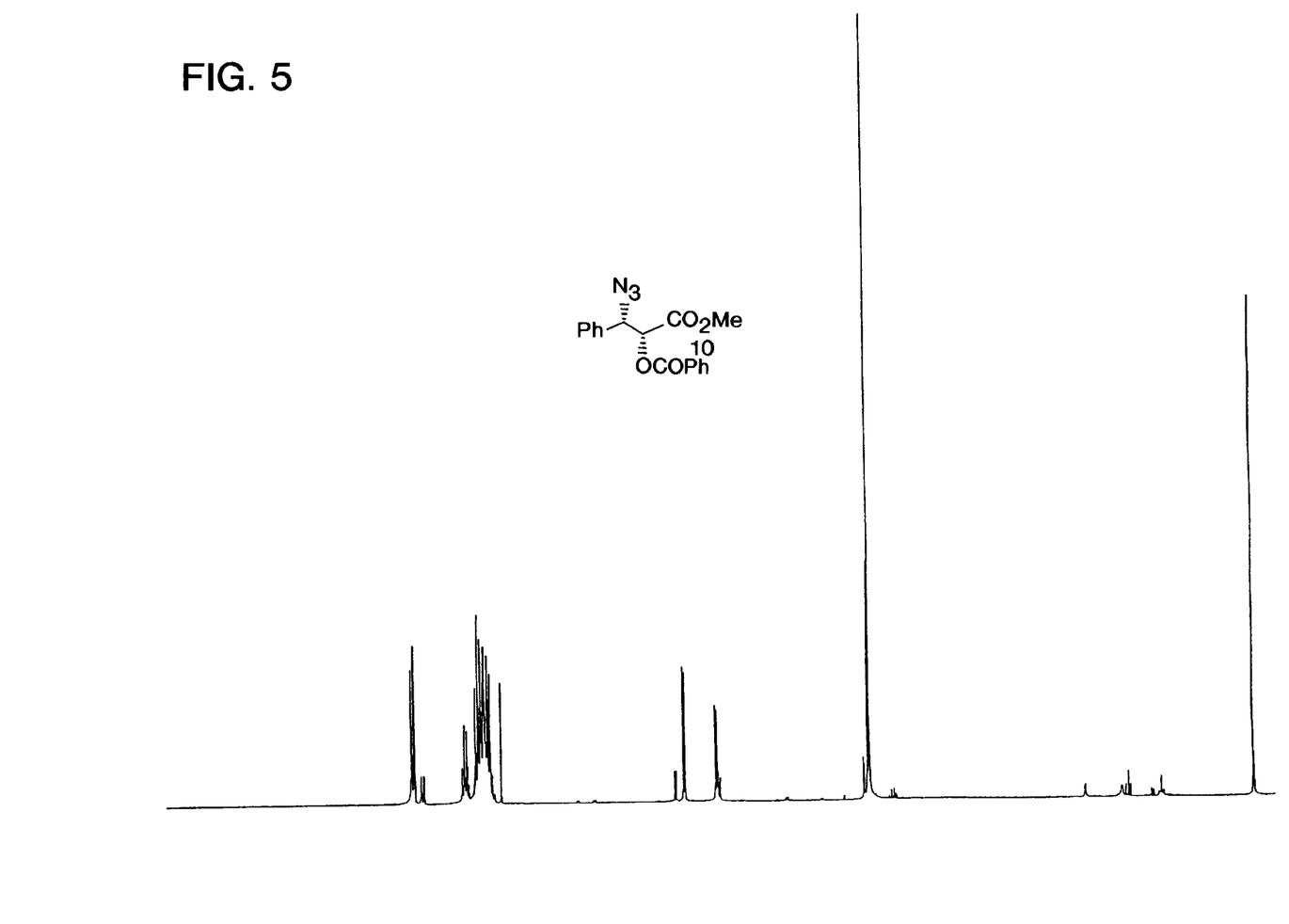
Figure 6:
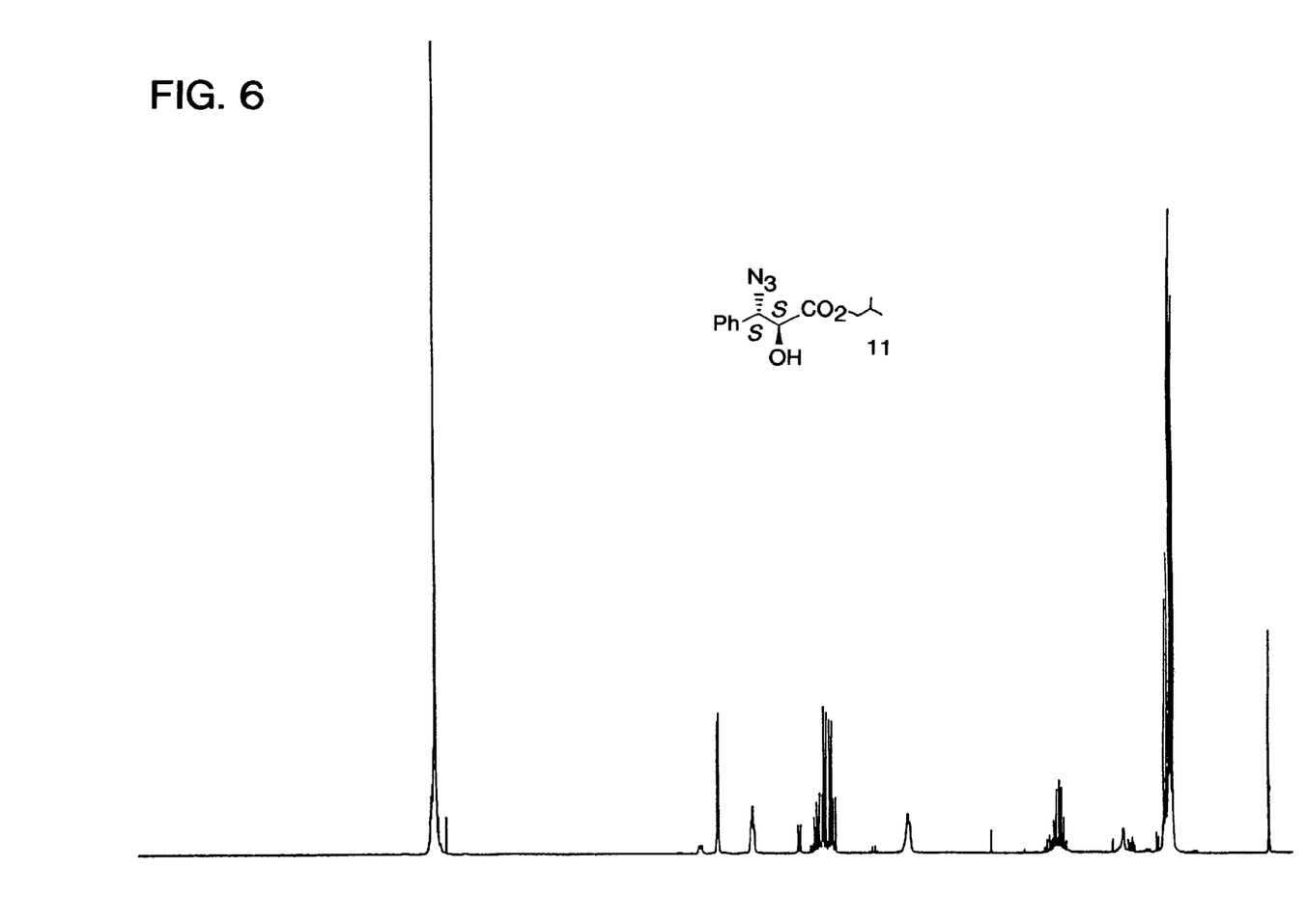
Figure 7:
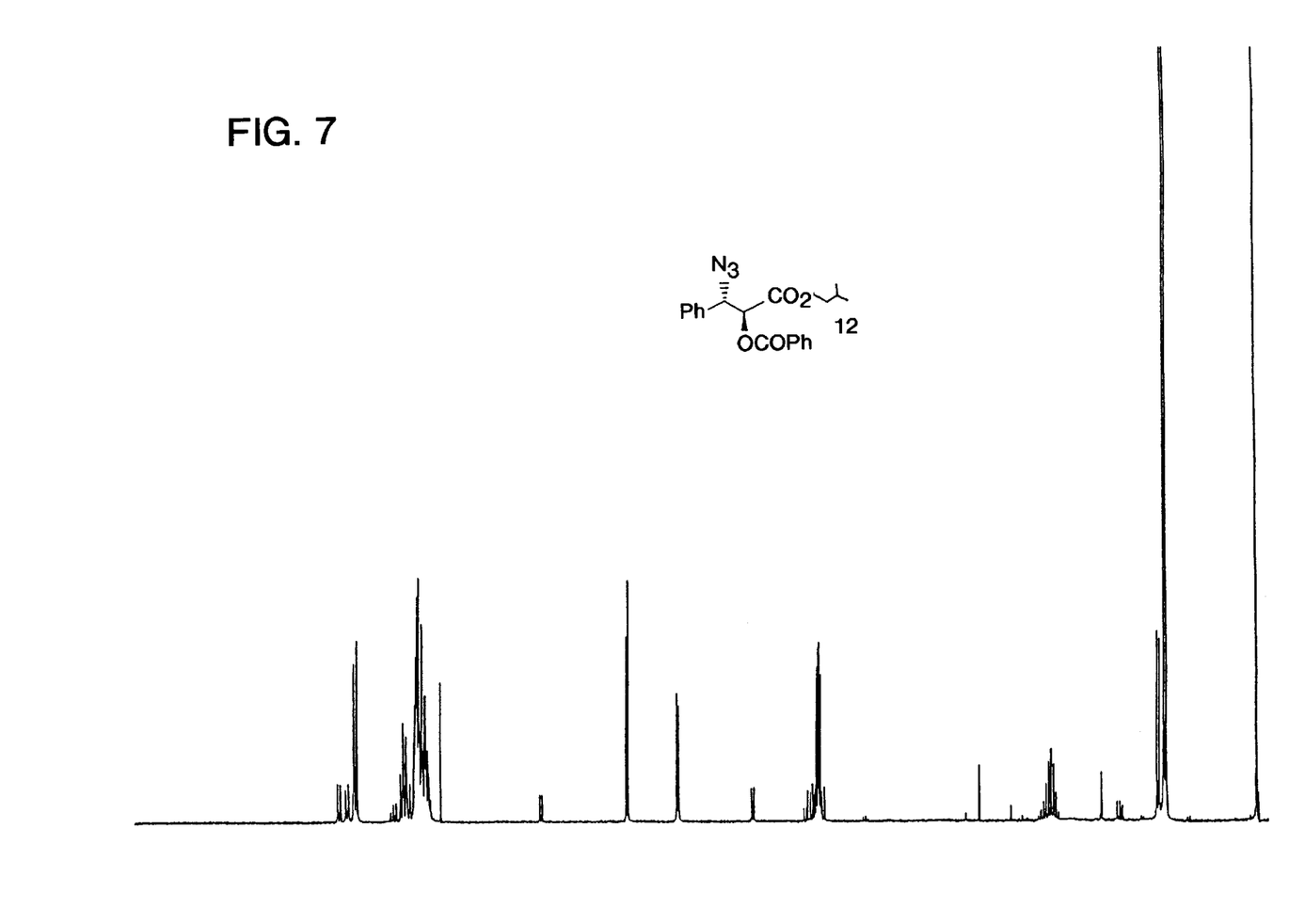
Figure 8:
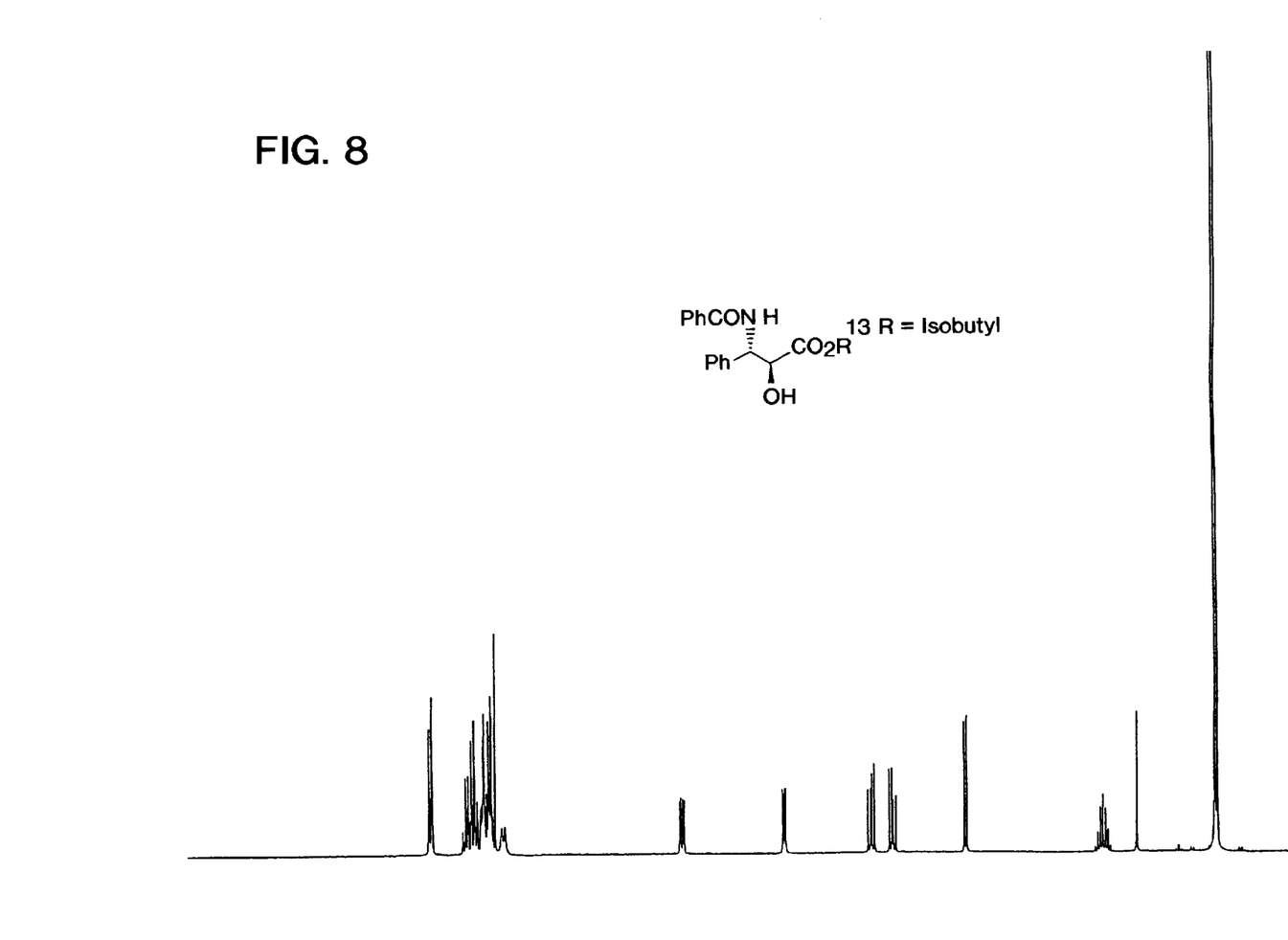
Figure 9:
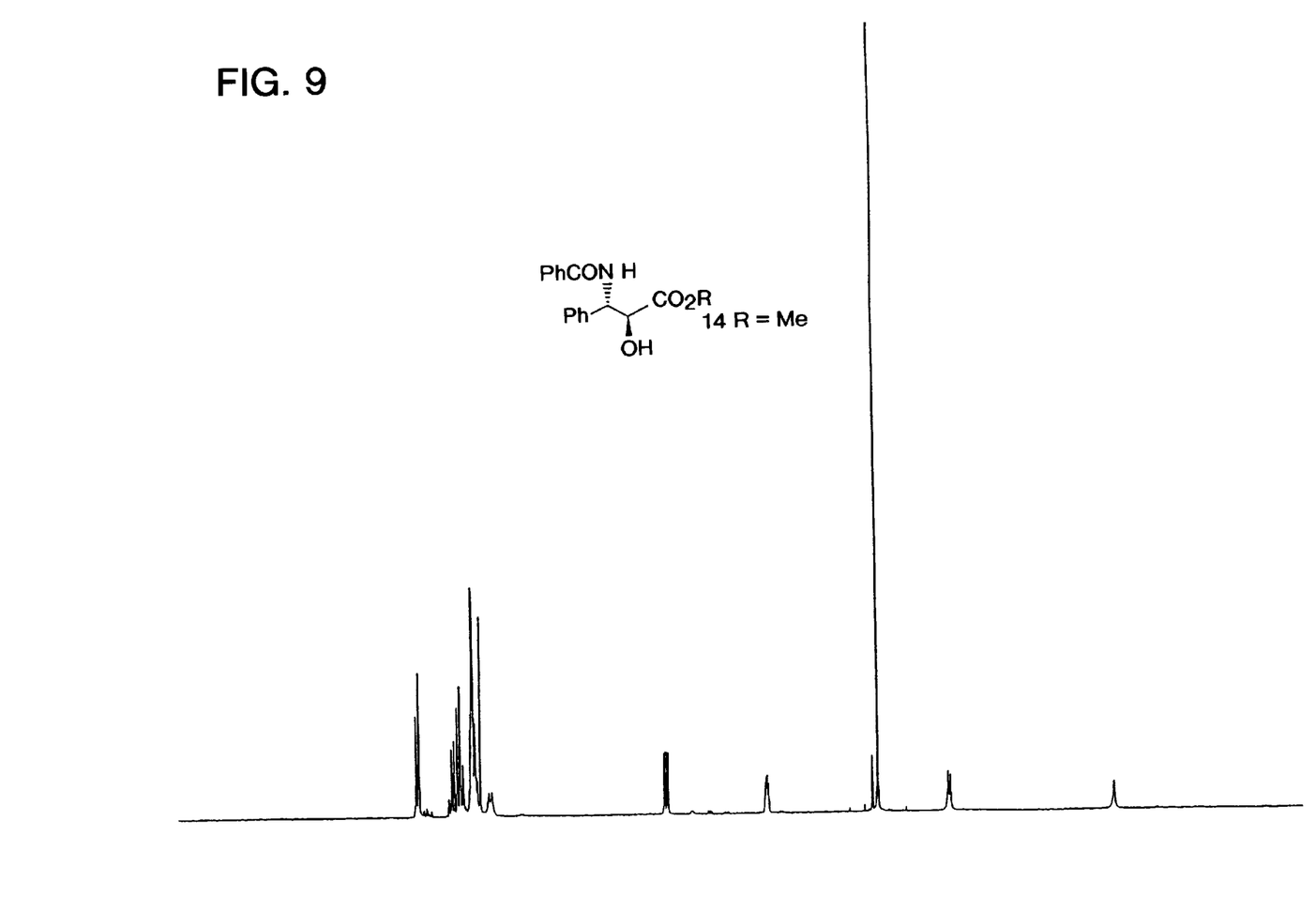
Figure 10:
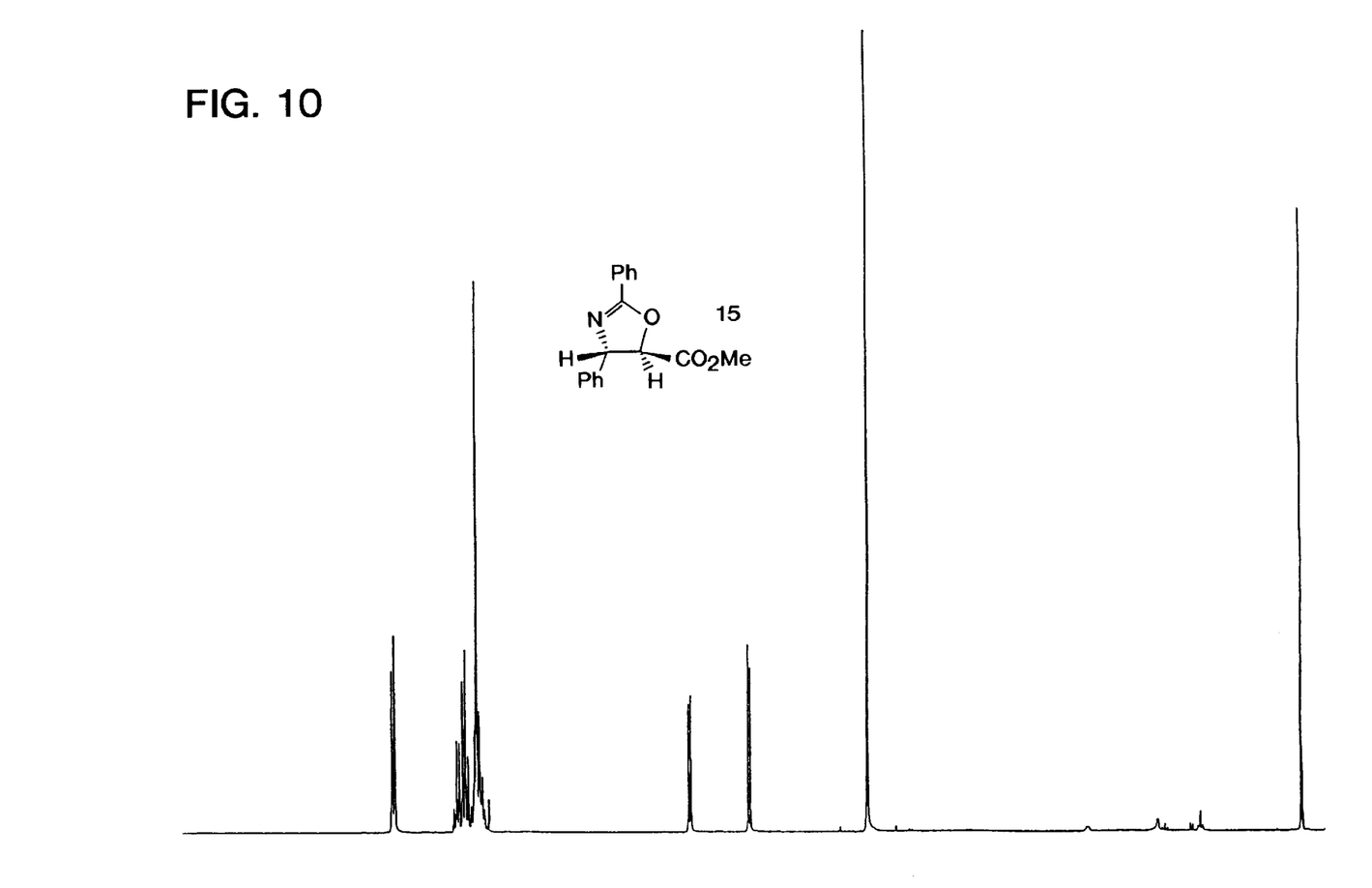
Figure 11:
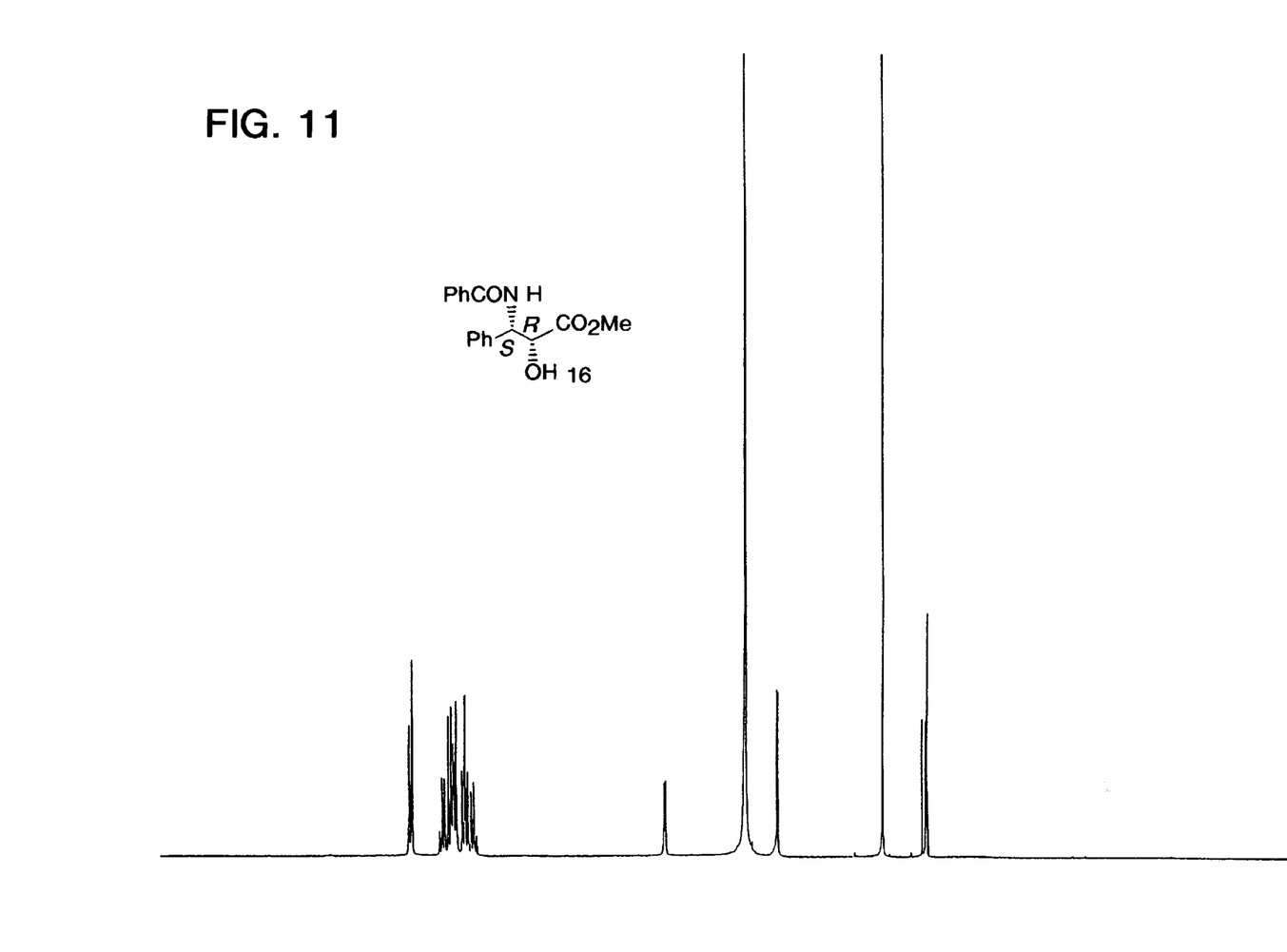

The resolution of methyl trans-β-phenylglycidate (±)–5 is achieved by lipase-mediated enantioselective transesterification in organic media, Chen, C. S.; Sih, C. J.; Angew.

Chem. Int. Ed. Engl., 1989, 28, 59. The racemic methyl ester is first exposed to different lipases in hexane with n-butyl alcohol as the acyl acceptor. Although all the enzymes tested were capable of mediating the formation of where R = butyl where R=butyl, Mucor miehei lipase (Amano, MAP-10) was uniquely suited to catalyze this stereospecific transesterification with high optical and chemical yields. Nevertheless, as noted in Table 1 below,

Zwanenbrurg, B., *Tetrahedron Lett.*, 1989, 30, 4881, (2R, 3S)-5, $[a]_D^{20}$=-173° ($CHCl_3$). [c]. Conversion (c) was calculated from the equation, c=ee(S)/[ee(S)+ee(P)], where ee(S) and ee(P) denote the values of enantiomeric excess of substrate and product fractions, Chen, C. C.; Fujimoto, Y.; Girdaukas, G.; Sih, C. J., *J. Am. Chem. Soc.*, 1982, 104, 7294. [d]. The enantiomeric excess was determined by $^1$H NMR analysis using a chiral shift reagent, Eu(hfc)$_3$. enantioselectivity of this acyl-transfer reaction appeared to be complicated by intrinsic thermodynamic equilibrium, of which the principle is well understood, Chen, C. S.; Wu, S. H.; Girdaukas, G.; Sih, C. J.; *J. Am. Chem. Soc.*, 1982, 104, 7294. The overall selectivity gradually diminishes as the reaction proceeds close to 50% conversion. Under these conditions, the kinetic and thermodynamic parameters were estimated to be E=33 and K=0.11. Considering the reversible biocatalyzed kinetic resolution,

TABLE 1

| Lipase | Stereo-preference[b] | Conversion[c] % (time) | Enantiomeric Excess[d] Substrate | Enantiomeric Excess[d] Product |
|---|---|---|---|---|
| ROH = butyl alcohol | | | | |
| Pseudomonas sp. lipase AK | 2S, 3R | 23 (12 h) | 19 | 64 |
| Pseudomonas sp. lipase P-30 | 2S, 3R | 41 (24 h) | 35 | 50 |
| Porcine pancreas lipase | 2S, 3R | 24 (48 h) | 12 | 38 |
| Candida cylindracea lipase | 2S, 3R | 37 (24 h) | 26 | 44 |
| Humicola lanuginisa lipase R-10 | 2R, 3S | 26 (36 h) | 11 | 32 |
| Mucor miehei lipase MAP-10 | 2S, 3R | 33 (23 h) | 46 | 91 |
| | | 41 (48 h) | 59 | 85 |
| | | 51 (82 h) | 77 | 78 |
| ROH = isobutyl alcohol | | | | |
| Mucor miehei lipase MAP-10 | 2S, 3R | 36 (24 h) | 56 | 97 |
| | | 45 (40 h) | 77 | 95 |

Table Legend

[a]. For the n-butyl alcohol experiments, all reactions were conducted with (±)-5 (1 g, 0.62 mmol), n-butyl alcohol (4.6 ml, 6.2 mmol), and the lipase (3 g) in water-saturated hexane (10 ml). The suspension was shaken (250 rpm) at 23° C. for the indicated time. The reaction was terminated by removing the enzyme powder through filtration. For the isobutyl alcohol experiments, the reaction was run with (±)-5 (20 g, 0.11 mmol), isobutyl alcohol (80 ml), and lipase MAP-10 (60 g) in hexane (80 ml). The mixture was incubated at 30° C. on a rotary shaker (250 rpm). [b]. lit., Legters, J.; Thijs, L.;

where $k_1$, $k_2$, $k_3$, and $k_4$ are apparents rate constants, $E=k_1/k_3$; $K=k_2/k_1$. A full account of this quantitative expression is described in Chen, supra. To minimize the extent of reverse catalysis, i.e. to reduce the K value, two strategies were employed, Chen, C. S.; Sih, C. J.; *Angew. Chem. Int. Ed. Engl.*, 1989, 28, 596, selecting a sterically hindered alcohol as the acyl acceptor and increasing the alcohol concentrations. It was found that the backward reaction became virtually negligible with isobutyl alcohol-hexane (1:1; v/v) as the reaction medium. For example, (±)-5 was incubated with Lipase MAP-10 in hexane-isobutyl alcohol (1:1). At 36% and 45% conversion, the enantiomeric excess (e.e.) values for the product fraction were 97%, and 95%, respectively; those for the remaining substrate fraction were 56%, and 77%, respectively. Thus, this enzymatic process coupled with substrate recycling afforded both fractions with e.e. greater than 95%.

(−)-5 and (+)-7 can be efficiently utilized to prepare the desired C-13 side chain methyl ester (16) as illustrated in the Scheme set forth below.

-continued a) $(C_2H_5)_2NH$——$HBr/(C_2H_5)_2AlCl/CH_2Cl_2$; b) $NaN_3/DMF$;
c) $PhCOCl/DMAP/CH_2Cl_2$; d) 10% Pd/C, $H_2$, $CH_3OH$;
e) $NaN_3/NH_4Cl/Acetone-H_2O$ (4:1); f) $Na_2CO_3/CH_3OH$——$H_2O$ (3:1);
g) $CH_2N_2$; h) $SOCl_2/CH_2Cl_2$; i) aq. 1N $HCl/CH_3OH$. The numbers inside the parentheses represent the $[\alpha]_D^{20}$ values. Optical rotations were determined in chloroform unless otherwise indicated.

Regioselective cleavage of the (2R,3S)-epoxide 5 with diethylamine hydrobromide, Gao, L. -X.; Saitoh, H.; Feng, F.; Murai, A.; *Chem. Lett.*, 1991, 1787, and diethyla uminum chloride yielded the (2R,3R)-hydroxy bromide (−)-8 in 90% yield. No appreciable formation of the (2R,3R)-epimer was detectable. Azide displacement of (+)-8 led to the C-3 inverted product (+)-9 in 80% yield. The hydroxy azide 9 was then subjected to benzoylation and hydrogenation in the usual manner, furnishing directly 16 in quantitative yield, 16: mp 181–183° C.; $[a]_D20_{=−49}°$ (c 1, $CH3OH$); lit. (ref. 7): $[a]D20=−49.6°$ (c 1, $CH3OH$). Recrystallization of the crude compound gave enantiomerically pure 16 with an overall yield of 50% from (−)-5. On the other hand, the use of (+)-7 could be made of by refluxing with sodium azide and ammonium chloride in acetone-water to afford the (2S,3S)-hydroxy azide (+)-11. Compound (+)-11 was subjected to benzoylation and then hydrogenation to yield the key intermediate (−)-13. To confirm the structure of the compound, the isobutyl ester was transformed to the corresponding methyl ester (−)-14 in 81% yield. The erythro-isomer 14 was treated with thionyl chloride to afford the oxazoline intermediate (+)-15, resulting in inversion of configuration at the C-2, (a) Johnson, W. S.; Schuber, E. N.; *J. Am. Chem. Soc.*, 1950, 72, 2187; (b) McCasland, G. E.; Smith, D. A.; *Ibid*, 1950, 72, 2190. Subsequent hydrolysis of (+)-15 with aqueous 1 N HCl in methanol, followed by recrystallization, yielded the enantiomerically pure thero-isomer 16 with an overall yield of 44% from (+)-7.

The synthetic method disclosed herein is straightforward, utilizes readily available materials and an inexpensive lipase and provides an expedient entry to the taxol C-13 side chain and its analogues.

EXAMPLE

Enantioselective Transesterification of (±)-5 with Isobutyl alcohol in Hexane by Mucor miehei Lipase MAP-10. Crude MAP-10 lipase (60 g powder, 4 g protein) was added to a mixture of (+)-5 (20 g, 0.11 mol) and isobutyl alcohol (80 ml) in hexane (80 ml). The resulting suspension was incubated at 30° C. on a rotary shaker (250 rpm). After 40 h, the reaction was terminated by removing the enzyme powder through filtration. The organic solvent was taken to dryness under reduced pressure, and the residue was chromatographed over a silica gel column (hexane-ethyl ether, 20:1) to afford (+)-7 {11.3 g; [a]D20=+129° (c 1.5, CHCl3); 95% e.e.} and (−)-5 {12.5 g; [a]D20=−133° (c 1.5, CHCl3); 77% e.e.}. The remaining substrate (12.5 g) was reincubated with lipase MAP-10 (12 g) in hexane-isobutyl alcohol (1:1, 30 ml). The reaction was stopped after 48 h according to the procedure described above to furnish (−)-5 {8.5 g; [a]D20=−163° (c 1.5, CHCl3); 95% e.e.}.

(2R,3R)-(−)-Methyl 3-bromo-2-hydroxy-3-phenylpropionate (8). A solution of (−)-5 ( 8.5 g, 48 mmol) in methylene chloride (100 ml) was added dropwise to a mixture of diethylamine hydrobromide (22.5 g, 71 mmol), diethylaluminum chloride (9 ml, 71 mmol), and methylene chloride (200 ml) at −41° C. The mixture was stirred at −15° C. for 2.5 h, washed with 1 N HCl and water, dried, and concentrated. Column chromatography (hexane-ether, 20:1→5:1) of the residue gave 8 (11 g, 90%): [a]D20=−138° (c 1.2, CHCl3); 1H NMR d 3.05 (d, J=9.6 Hz, 1H), 3.73 (s, 1 H), 4.70 (dd, J=4.8, 6.8 Hz, 1 H), 5.26 (d, J=4.5 Hz, 1 H), 7.29–7.46 (m, 5 H).

(2R,3S)-(+)-Methyl 3-azido-2-hydroxy-3-phenylpropionate (9). A mixture of (−)-8 (10 g, 38 mmol), sodium azide (10 g, 155 mmol), and DMF (40 ml) was stirred at 65–75° C. for 40 h. The solution was diluted with ethyl acetate (200 ml), washed with water, dried, and concentrated. Column chromatography (hexane-ether, 25:1→5:1) of the residue afforded 9 (6.9 g, 80%):[a]D20=+107° (c 1.2, CHCl3); 1H NMR d 3.09 (d, J=6.6 Hz, 1H), 3.79 (s, 3H), 4.34 (dd, J=4.8, 6.6 Hz, 1H), 4.83 (d, J=4.8 Hz, 1 H), 7.27–7.43 (m, 5H).

(2R,3S)-(+)-Methyl 3-azido-2-benzoxy-3-phenylpropionate (10). A solution of (+)-9 (7.5 g, 34 mmol) and 4-dimethylaminopyridine (4.15 g, 34 mmol) in methylene chloride (50 ml) was treated with benzoyl chloride (4.2 ml, 34 mmol) at 23° C. for 1 h. The reaction mixture was processed in the usual manner. Column chromatography (hexane-ether, 25:1→5:1) of the residue furnished 10 (10.3 g, 93%):[ ]D20=+98° (c 1, CHCl3); 1H NMR d 3.69 (s, 3 H), 5.17 (d, J=4.8 Hz, 1 H), 5.49 (d, J=4.8 Hz, 1 H), 7.32–7.61 (m, 8 H), 7.98–8.11 (m, 2 H).

(2R,3S)-(−)-N-Benzoyl-3-phenylisoserine methyl ester (16). The azide 10 (10 g, 24 mmol) was hydrogenated with 10% Pd/C (2.5 g) in methanol under H2 (50 p.s.i.) for 4 h. The solution was filtered, stood at 23° C. for 48 h, and concentrated. The solid was recrystallized over chloroform-methanol (50:1) to give 16 (5.5 g, 74%):[a]D20=−49 (c 1, CH3OH), lit. [a]D20=−49.6° (c 1, CH3OH); 1H NMR (CD3OD) d 3.68 (s, 3H), 4.60 (d, J=3.8 Hz, 1 H), 5.58 (d, J 3.8 Hz, 1 H), 7.32–7.61 (m, 8 H), 7.98–8.11 (m, 2 H).

Anal. Calcd for C17H17NO4:C, 68.21; H, 5.73; N, 4.68. Found:C, 68.42; H, 5.92; N, 4.76.

(2S,3S)-(+)-Isobutyl 3-azido-2-hydroxy-3-phenylpropionate (11). A solution of the (2S,3R)-epoxide 7 (11.2 g, 50 mmol), sodium azide (8.13 g, 125 mmol) and ammonium chloride (10 g, 18.7 mmol) in acetone/water (4:1, 250 ml) was stirred under reflux for 20 h. The reaction mixture was processed with methylene chloride in the usual manner. Column chromatography (25:1→5:1) of the residue afforded (+)-11 (12.7 g, 95%):[a]D20=+55° (c 1.1, CHCl3); 1H NMR d 0.93 (d, J=9 Hz, 6 H), 1.93–2.07 (m, 1 H), 3.15 (d, J=5.7 Hz, 1 H), 3.79–4.01 (m, 2 H), 4.52–4.55 (m, 1 H), 4.86 (d, J=5.7 Hz, 1 H), 7.27–7.41 (m, 5 H).

(2S,3S)-(+)-Isobutyl 3-azido-2-benzoxy-3-phenylpropionate (12). Compound 11 (12.6 g, 47 mmol) was benzoylated, as described for 10, to yield (+)-12 (16 g, 88%):[a]D20=+54° (c 2, CHCl3); 1H NMR d 0.93 (d, J=9 Hz, 6 H), 1.75–1.91 (m, 1 H), 3.84–3.90 (m, 2 H), 5.15 (d, J=6 Hz, 1 H), 5.60 (d, J=6 Hz, 1 H), 7.34–7.61 (m, 8 H), 7.99–8.03 (m, 2 H).

(2S,3S)-(−)-Isobutyl N-benzoyl-phenylisoserine (13). Conventional hydrogenation of 12 (15.5 g, 42 mmol), as described for 16, gave (−)-13 (13.5 g, 90%):[a]D20=−38° (c 1, CHCl3); 1H NMR d 0.93 (d, J=9 Hz, 6 H), 1.87–2.00 (m, 1 H), 3.13 (d, J=6.3 Hz, 1 H), 3.86 (m, 2 H), 4.73 (dd, J=4, 6.3 Hz, 1 H), 5.46 (dd, J=4, 6.3 Hz, 1 H), 7.2 (d, J=6 Hz, 1 H), 7.27–7.74 (m, 8 H), 7.81–7.84 (m, 2 H).

Anal. Calcd for C20H23NO4: C, 70.36; H, 6.79; N, 4.10. Found: C, 70.40; H, 6.79; N, 4.05.

(2S,3S)-(−)-Methyl N-benzoyl-phenylisoserine (14). A mixture of the butyl ester 13 (13.4 g, 39 mmol), sodium carbonate (6 g, 56 mmol), and 75% aqueous methanol was stirred at 23° C. for 4 h. The solution was concentrated, diluted with water (150 ml), and extracted with methylene chloride. The aqueous layer was acidified to pH 1, and extracted with ethyl acetate (40 ml×3). The combined ethyl acetate fractions were washed with water, dried, and treated with diazomethane. Recrystallization (from methylene chloride-methanol, 50:1) of the residue afforded (−)-14 (9.6 g, 81%):[a]D20=−23° (c 1, CHCl3); 1H NMR d 3.11 (d, J=6 Hz, 1 H), 3.74 (s, 3 H), 4.71 (dd, J 3, 6 Hz, 1 H), 5.66 (dd, J=3, 6 Hz, 1 H), 7.18–7.55 (m, 8 H), 7.81–7.84 (m, 2 H).

Anal. Calcd. for C17H17NO4: C, 68.21; H, 5.73; N, 4.68. Found: C, 68.21; H, 5.65; N, 4.69.

(4S,5R)-(+)-2,4-diphenyl-5-(methoxycarbonyl)-2-oxazoline (15). A solution of (−)-14 (9.5 g, 31 mmol) and thionyl chloride (6 ml, 79 mmol) in chloroform (40 ml) was stirred at 45° C. for 5 h. The solution was concentrated, dissolved in chloroform (40 ml), and refluxed for 48 h. The solution was washed with water, dried, and concentrated. Column chromatography (hexane-ether, 25:1→5:1) of the residue furnished (+)-9 (6.5 g, 73%):[a]D20=+13° (c 1, CHC3); 1H NMR d 3.84 (s, 3 H), 4.91 (d, J=6 Hz, 1 H), 5.45 (d, J=6 Hz, 1 H), 7.29 (m, 8 H), 8.08 (m, 2 H).

(2R,3S)-(−)-N-Benzoyl-3-phenylisoserine methyl ester (16). The oxazoline (+)-15 (6.2 g, 22 mmol) was hydrolyzed by refluxing 1 N HCl (22 ml) in methanol (65 ml) for 2 h. The solution was processed with methylene chloride in the usual manner. Recrystallization (methylene chloride-methanol, 25:1→5:1) of the residue gave (−)-16 (5.3 g, 80%). The physical data were identical to those aforementioned for the compound 16 derived from (+)-5.

The foregoing description has been limited to specific embodiments of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A method for the production of a compound of Formula (I)

where R=H or CH3 comprising:

incubating:

with *Mucor miehei* lipase MAP-10 in the presence of isobutyl alcohol/hexane in an amount sufficient to produce the reaction products;

separating the reaction products; regioselectively cleaving and displacing substituents of said separated reaction products; benzoylating said cleaved and displaced products; hydrogenating said benzoylated products to produce the compound of Formula (I); and recovering the compound of Formula (I).

2. The method according to claim 1 which comprises: regioselectively cleaving (5) to form

3. The method according to claim 2 which comprises: displacing the substituent Br of (8) to form

4. The method according to claim 3 which comprises: benzoylating (9) to form 5. The method according to claim 4 which comprises: hydrogenating (10) to form 6. The method according to claim 1 which comprises refluxing (7) to form wherein R=isobutyl.

7. The method of claim 6 which comprise benzoylating (11) to form wherein R=isobutyl.

8. The method of claim 7 which comprises hydrogenating (12) to form wherein R=isobutyl.

9. The method of claim 8 which comprises transforming (13) to form wherein R=Me.

10. The method of claim 9 which comprises refluxing (14) to form (15)

11. The method of claim 10 which comprises hydrolyzing and subsequently recrystallizing (15) to form (16).

* * * * *